(12) United States Patent
Yoshiara et al.

(10) Patent No.: US 10,575,826 B2
(45) Date of Patent: Mar. 3, 2020

(54) ULTRASOUND DIAGNOSTIC APPARATUS AND ULTRASOUND IMAGING METHOD

(71) Applicant: Toshiba Medical Systems Corporation, Otawara-shi (JP)

(72) Inventors: Hiroki Yoshiara, Nasushiobara (JP); Kuramitsu Nishihara, Otawara (JP); Akihiro Kakee, Nasushiobara (JP); Tetsuya Kawagishi, Nasushiobara (JP); Makoto Hirama, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 906 days.

(21) Appl. No.: 14/558,015

(22) Filed: Dec. 2, 2014

(65) Prior Publication Data

US 2015/0087985 A1    Mar. 26, 2015

Related U.S. Application Data

(63) Continuation of application No. PCT/JP2013/065587, filed on Jun. 5, 2013.

(30) Foreign Application Priority Data

Jun. 5, 2012 (JP) .................................. 2012-128051

(51) Int. Cl.
    *A61B 8/08* (2006.01)
    *G01S 7/52* (2006.01)
    (Continued)

(52) U.S. Cl.
    CPC .............. *A61B 8/5246* (2013.01); *A61B 8/14* (2013.01); *A61B 8/481* (2013.01); *A61B 8/5207* (2013.01);
    (Continued)

(58) Field of Classification Search
    CPC ....... A61B 8/5246; A61B 8/5253; A61B 8/14; A61B 8/481; A61B 8/5238; A61B 8/5207;
    (Continued)

(56) References Cited

U.S. PATENT DOCUMENTS 6,602,195 B1    8/2003    Krishnan et al.
6,682,482 B1    1/2004    Krishnan
(Continued)

FOREIGN PATENT DOCUMENTS

CN          1500445 A          6/2004
JP       2013-056033 A1        3/2013

OTHER PUBLICATIONS

International Search Report dated Jul. 16, 2013 for PCT/JP2013/065587 filed on Jun. 5, 2013 with English Translation.
(Continued)

*Primary Examiner* — Katherine L Fernandez
(74) *Attorney, Agent, or Firm* — Oblon, McClelland, Maier & Neustadt, L.L.P.

(57) ABSTRACT

An ultrasound diagnostic apparatus according to an embodiment includes a transmitter/receiver, an adder/subtractor and an image generating unit. The transmitter/receiver performs a first set of ultrasound transmission/reception and a second set of ultrasound transmission/reception, on a same scanning line of an imaging region of a subject administered with a contrast agent, for a plurality of sets, to output reflected wave data for the plurality of sets, the first set of the ultrasound transmission/reception performing amplitude-modulated or amplitude- and phase-modulated ultrasound transmission transmitted a plurality of times and receiving reflected waves, and the second set of the ultrasound transmission/reception being transmission/reception whose phase modulation being different from phase modulation of
(Continued)

the first set of the ultrasound transmission/reception. The adder/subtractor adds or subtracts the reflected wave data for the plurality of the sets. The image generating unit generates contrast image data based on the data output from the adder/subtractor.

11 Claims, 11 Drawing Sheets

(51) Int. Cl.
*G01S 15/89* (2006.01)
*A61B 8/14* (2006.01)
(52) U.S. Cl.
CPC ...... *G01S 7/52038* (2013.01); *G01S 7/52046* (2013.01); *G01S 15/8963* (2013.01)
(58) Field of Classification Search
CPC ............. G01S 7/52038; G01S 7/52039; G01S 7/52046; G01S 15/8963
See application file for complete search history.

(56) References Cited

U.S. PATENT DOCUMENTS

| | | |
|---|---|---|
| 6,783,496 B2 | 8/2004 | Hao et al. |
| 2004/0087857 A1* | 5/2004 | Napolitano ......... G01S 7/52039 600/443 |
| 2005/0256404 A1* | 11/2005 | Sato ....................... A61B 8/481 600/437 |
| 2011/0040183 A1* | 2/2011 | Yoshida ............. G01N 29/0672 600/443 |

OTHER PUBLICATIONS

International Written Opinion dated Jul. 16, 2013 for PCT/JP2013/065587 filed on Jun. 5, 2013.
Combined Office Action and Search Report dated Feb. 9, 2015 in Chinese Patent Application No. 201380000862.8 with English translation of category of cited documents.

* cited by examiner

ULTRASOUND DIAGNOSTIC APPARATUS AND ULTRASOUND IMAGING METHOD

CROSS-REFERENCE TO RELATED APPLICATION(S)

This application is a continuation of PCT international application Ser. No. PCT/JP2013/065587 filed on Jun. 5, 2013 which designates the United States, incorporated herein by reference, and which claims the benefit of priority from Japanese Patent Application No. 2012-128051, filed on Jun. 5, 2012, the entire contents of which are incorporated herein by reference.

FIELD

Embodiments described herein relate generally to an ultrasound diagnostic apparatus and an ultrasound imaging method.

BACKGROUND

In recent years, intravenously administered ultrasound contrast agents have been commercialized, and a contrast echo technique called contrast harmonic imaging (CHI) has been performed using ultrasound diagnostic apparatuses. Contrast echo techniques are intended for evaluation of hemodynamics by intravenously infusing ultrasound contrast agents to enhance blood-flow signals in cardiac and hepatic tests, for example. Many types of ultrasound contrast agents have microbubbles serving as a reflection source. However, due to its delicate nature as the base material, bubbles are broken by the mechanical action of ultrasound waves, resulting in reduction in the intensity of signals from the scanned surface, even when the ultrasound waves are irradiated at the level of ordinary diagnosis.

For the above reason, to observe the dynamic state of reflux flow in real time, it is necessary to relatively reduce the breakdown of the bubbles due to scanning by performing imaging with transmission of ultrasound waves with low acoustic pressure, for example. During such imaging with transmission of ultrasound waves with low acoustic pressure, the signal/noise (S/N) ratio is lowered. To compensate this, various signal processing methods have been developed such as phase modulation (PM), amplitude modulation (AM), and amplitude modulation/phase modulation (AMPM). The above-mentioned imaging methods enable real-time display of a contrasted image with a high S/N ratio. Ultrasound contrast imaging is used for detailed examination of microstructures (microvascular structures, for example) that cannot be visualized by X-ray computed tomography (CT) apparatuses or magnetic resonance imaging (MRI) apparatuses in view of real-time performance and high spatial resolution. Ultrasound contrast imaging may also be useful for differential diagnosis because it enables observation of irregular courses of tumor vessels and nutrient vessels. Ultrasound contrast imaging is used for superficial regions in addition to abdominal regions.

When observing a microlesion, an ultrasonic probe with high frequency (6 MHz or higher) is used to obtain spatial resolution although it reduces sensitivity in a deep region. When scanning a patient with a thick abdominal wall also, depth sensitivity is reduced. This is because the ultrasound waves transmitted with high frequency causes significant frequency-dependent attenuation, and thereby the observable region (penetration) is limited to a shallow area. To secure an observation depth, frequency is lowered generally although it lowers spatial resolution. Clinically, it is necessary to observe a lesion with the spatial resolution being maintained in the deep region. However, this may not be satisfied in some cases.

DETAILED DESCRIPTION

An ultrasound diagnostic apparatus according to an embodiment includes a transmitter/receiver, an adder/subtractor and an image generating unit. The transmitter/receiver performs a first set of ultrasound transmission/reception and a second set of ultrasound transmission/reception, on a same scanning line of an imaging region of a subject administered with a contrast agent, for a plurality of sets, to output reflected wave data for the plurality of the sets, the first set of the ultrasound transmission/reception performing amplitude-modulated or amplitude- and phase-modulated ultrasound transmission transmitted a plurality of times and receiving reflected waves, and the second set of the ultrasound transmission/reception being transmission/reception whose phase modulation being different from phase modulation of the first set of the ultrasound transmission/reception. The adder/subtractor adds or subtracts the reflected wave data for the plurality of the sets. The image generating unit generates contrast image data based on the data output from the adder/subtractor.

An ultrasound diagnostic apparatus according to embodiments will be explained in detail below with reference to accompanying drawings.

First Embodiment

The configuration of an ultrasound diagnostic apparatus according to a first embodiment will be first described. FIG.

Figure 1:
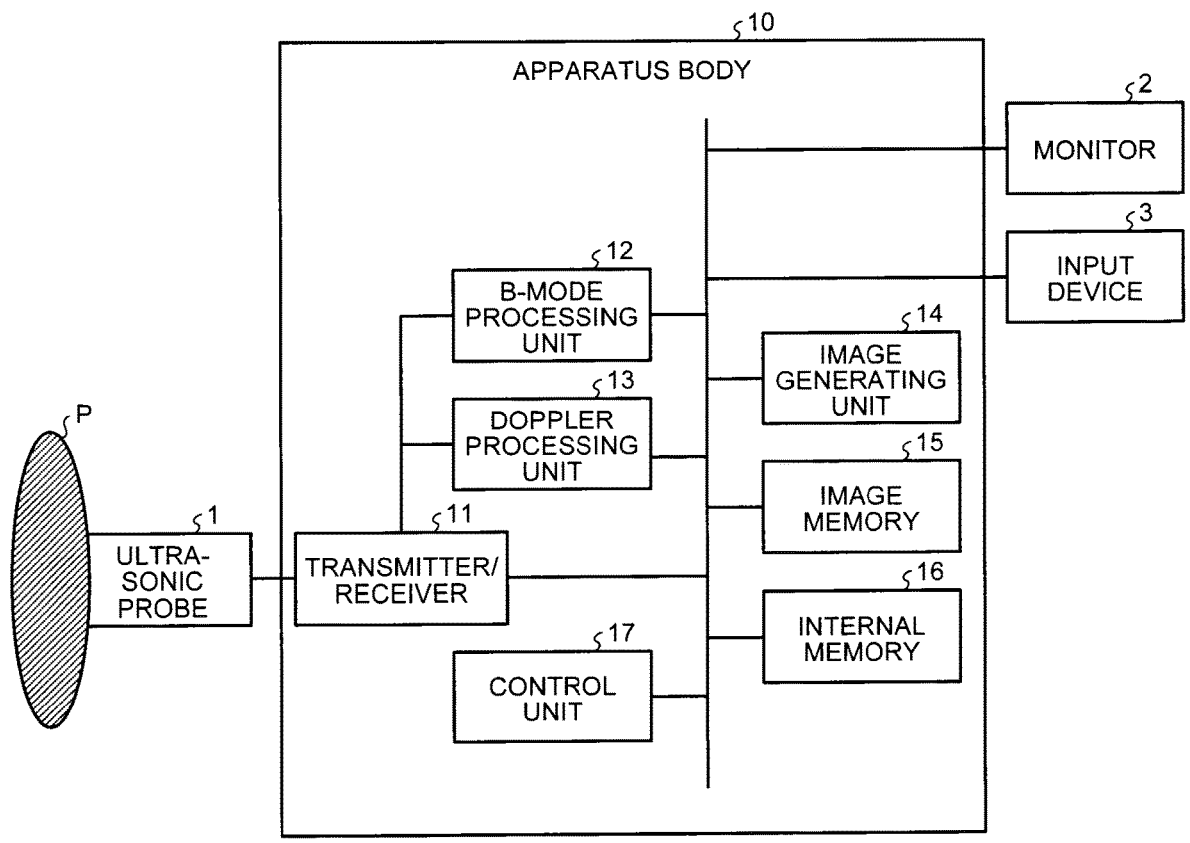
FIG. 1 is a block diagram illustrating a configuration example of an ultrasound diagnostic apparatus according to a first embodiment.

1 is a block diagram illustrating a configuration example of the ultrasound diagnostic apparatus according to the first embodiment. As illustrated in FIG. 1, the ultrasound diagnostic apparatus according to the first embodiment includes an ultrasonic probe 1, a monitor 2, an input device 3, and an apparatus body 10.

The ultrasonic probe 1 includes a plurality of piezoelectric transducer elements. The plurality of the piezoelectric transducer elements generate ultrasonic waves based on a drive signal supplied from a transmitter/receiver 11 included in the apparatus body 10 described later. The plurality of the piezoelectric transducer elements included in the ultrasonic probe 1 receive a reflected wave from a subject P to convert the reflected wave thus received into an electric signal. The ultrasonic probe 1 also includes matching layers provided to the piezoelectric transducer elements and backing materials preventing ultrasonic waves from traveling behind the piezoelectric transducer elements, for example. The ultrasonic probe 1 is removably connected to the apparatus body 10.

When ultrasonic waves are transmitted from the ultrasonic probe 1 to the subject P, the ultrasonic waves thus transmitted are sequentially reflected on the planes of discontinuity of acoustic impedances in body tissues of the subject P and then received by the plurality of the piezoelectric transducer elements included in the ultrasonic probe 1 as reflected wave signals. The amplitudes of the reflected wave signals thus received depend on the differences of the acoustic impedances on a plane of discontinuity on which the ultrasonic waves are reflected. When the ultrasonic pulses transmitted are reflected on a moving blood flow or the surface of a cardiac wall, for example, the reflected wave signals undergoes a frequency shift depending on the velocity component in the ultrasound transmission direction of the moving body because of the Doppler effect.

For the ultrasonic probe 1 according to the first embodiment, one-dimensional array probe two-dimensionally scanning the subject P and a mechanical four-dimensional probe and a two-dimensional array probe three-dimensionally scanning the subject p are applicable.

An input device 3 includes a mouse, a keyboard, buttons, a panel switch, a touch command screen, a foot switch, a track ball, or a joystick, and the like. The input device 3 receives various setting requests from the operator of the ultrasound diagnostic apparatus and transmits the setting requests thus received to the apparatus body 10.

The monitor 2 displays a graphical user interface (GUI) through which the operator of the ultrasound diagnostic apparatus inputs various setting requests using the input device 3 and displays ultrasonic image data generated by the apparatus body 10, for example.

The apparatus body 10 is an apparatus that generates ultrasonic image data based on the reflected wave signal received by the ultrasonic probe 1. The apparatus body 10 illustrated in FIG. 1 is an apparatus that can generate two-dimensional ultrasonic image data based on two-dimensional reflected wave signals. The apparatus body 10 illustrated in FIG. 1 also is an apparatus that can generate three-dimensional ultrasonic image data based on three-dimensional reflected wave signals. However, in the first embodiment, a case is applicable where the apparatus body 10 is an apparatus dedicated for two-dimensional data.

The apparatus body 10 includes the transmitter/receiver 11, a B-mode processing unit 12, a Doppler processing unit 13, an image generating unit 14, and an image memory 15, an internal memory 16, a control unit 17 as illustrated in FIG. 1.

The transmitter/receiver 11 controls ultrasound transmission/reception performed by the ultrasonic probe 1 based on an instruction from the control unit 17 described later. The transmitter/receiver 11 includes a pulse generator, a transmission delay unit, a pulser, and the like and supplies a drive signal to the ultrasonic probe 1. The pulse generator repeatedly generates a rate pulse for forming an ultrasonic wave for transmission at a predefined rate frequency. The transmission delay unit provides each rate pulse generated by the pulse generator with a delay time for each piezoelectric transducer element. The delay time is required to focus ultrasonic waves generated by the ultrasonic probe 1 into a beam and to determine transmission directivity. The pulser applies a drive signal (drive pulse) to the ultrasonic probe 1 at the timing based on the rate pulse. In other words, the transmission delay unit adjusts the transmission direction of the ultrasound wave transmitted from the surface of the piezoelectric transducer elements as required by changing the delay time provided to each rate pulse.

The transmitter/receiver 11 has functions capable of instantaneously changing transmission frequencies, transmission drive voltages, and the like in order to perform a predefined scan sequence based on an instruction from the control unit 17 described later. In particular, the transmission drive voltages can be changed with a linear amplifier type of oscillating circuit capable of instantaneously changing values or a mechanism electrically switching over a plurality of power source units.

The transmitter/receiver 11 includes an amplifier circuit, an analog/digital (A/D) converter, and a reception delay circuit, an adder, and a quadrature detection circuit, and performs various processing on the reflected wave signals received by the ultrasonic probe 1 to generate reflected wave data. The amplifier circuit amplifies the reflected wave signals for each channel and perform thereon gain correction processing. The A/D converter A/D-converts the reflected wave signals thus gain-corrected. The reception delay circuit provides digital data with a reception delay time required to determine reception directionality. The adder performs addition processing on the reflected wave signals provided with the reception delay time by the reception delay circuit. The addition processing performed by the adder enhances reflection components from the direction in accordance with the reception directionality of the reflected wave signals. The quadrature detection circuit converts an output signal from the adder into an in-phase (I) signal and a quadrature-phase (Q) signal in a baseband bandwidth. The quadrature detection circuit then stores the I signal and the Q signal (hereinafter, IQ signal) in a frame buffer (not illustrated) as reflected wave data. The quadrature detection circuit may convert an output signal from the adder into a radio frequency (RF) signal and store the output signal thus converted in a frame buffer (not illustrated).

The transmitter/receiver 11 causes the ultrasonic probe 1 to transmit two-dimensional ultrasonic beams when the subject P is two-dimensionally scanned. The transmitter/receiver 11 then generates two-dimensional reflected wave data from two-dimensional reflected wave signals received by the ultrasonic probe 1. The transmitter/receiver 11 also causes the ultrasonic probe 1 to transmit three-dimensional ultrasonic beams when the subject P is three-dimensionally scanned. The transmitter/receiver 11 then generates three-dimensional reflected wave data from three-dimensional reflected wave signals received by the ultrasonic probe 1.

The B-mode processing unit 12 and the Doppler processing unit 13 are signal processing units performing various signal processing on reflected wave data that the transmitter/ receiver 11 generated from reflected wave signals. The B-mode processing unit 12 receives reflected wave data from the transmitter/receiver 11 and performs logarithmic amplification, envelope demodulation, and the like to generate data (B-mode data) in which the intensity of a signal is represented by the brightness of its luminance. The Doppler processing unit 13 performs frequency analysis of velocity information from the reflected wave data received from the transmitter/receiver 11 and generates data (Doppler data) in which moving body information such as velocity, dispersion, power, and the like affected by the Doppler effect are extracted at multiple points. The moving body described above includes blood flows, tissues such as cardiac walls, and a contrast agent. The B-mode processing unit 12 and the Doppler processing unit 13 acquire reflected wave data through the frame buffer described above.

The B-mode processing unit 12 and the Doppler processing unit 13 illustrated in FIG. 1 can process both two-dimensional reflected wave data and three-dimensional reflected wave data. Specifically, the B-mode processing unit 12 generates two-dimensional B-mode data from two-dimensional reflected wave data and three-dimensional B-mode data from three-dimensional reflected wave data. The Doppler processing unit 13 generates two-dimensional Doppler data from two-dimensional reflected wave data and three-dimensional Doppler data from three-dimensional reflected wave data.

The image generating unit 14 generates ultrasonic wave image data from the data generated by the B-mode processing unit 12 and the Doppler processing unit 13. Specifically, the image generating unit 14 generates two-dimensional B-mode image data in which the intensity of a reflected wave is represented by the luminance from the two-dimensional B-mode data generated by the B-mode processing unit 12. The image generating unit 14 also generates two-dimensional Doppler image data representing moving body information from the two-dimensional Doppler data generated by the Doppler processing unit 13. The two-dimensional Doppler image data includes velocity image data, dispersion image data, power image data, or image data in which the data mentioned above are combined.

The image generating unit 14 typically generates ultrasonic image data for display through conversion (scan-conversion) of signal arrays of ultrasonic scanning lines into signal arrays of scanning lines in a video format represented by television, for example. Specifically, the image generating unit 14 generates ultrasonic image data for display through coordinate conversion in accordance with the form of the ultrasonic scan performed by the ultrasonic probe 1. The image generating unit 14 also performs various image processing other than the scan conversion. For example, the image generating unit 14 uses a plurality of image frames after the scan conversion to perform image processing reproducing an image having an average luminance (smoothing processing) and image processing using a differentiation filter in an image (edge enhancement processing). The image generating unit 14 also combines text information on various parameters, scales, body marks, and the like with ultrasonic image data.

The B-mode data and the Doppler data are ultrasonic image data before the scan conversion, and data generated by the image generating unit 14 is ultrasonic image data for display after the scan conversion. The B-mode data and the Doppler data are also referred to as raw data. The image generating unit 14 generates two-dimensional ultrasonic image data for display from two-dimensional ultrasonic image data before the scan conversion.

The image generating unit 14 further generates three-dimensional B-mode image data by performing coordinate conversion on the three-dimensional B-mode data generated by the B-mode processing unit 12. The image generating unit 14 also generates three-dimensional Doppler image data by performing coordinate conversion on the three-dimensional Doppler data generated by the Doppler processing unit 13. In other words, the image generating unit 14 generates "three-dimensional B-mode image data and three-dimensional Doppler image data" as "three-dimensional ultrasonic image data (volume data)".

The image generating unit 14 further performs rendering processing on volume data to generate various two-dimensional image data for causing the monitor 2 to display volume data. The rendering processing performed by the image generating unit 14 includes processing performing multi-planer reconstruction (MPR) to generate MPR image data from volume data. The rendering processing performed by the image generating unit 14 also includes volume rendering (VR) processing generating two-dimensional image data on which three-dimensional information is reflected.

The image memory 15 is a memory storing therein image data for display generated by the image generating unit 14. The image memory 15 also can store therein data generated by the B-mode processing unit 12 and the Doppler processing unit 13. The B-mode data and the Doppler data stored in the image memory 15 can be called by the operator after diagnosis, for example, and serve as ultrasonic image data for display after going through the image generating unit 14. The image memory 15 also can store therein the reflected wave data output from the transmitter/receiver 11.

The internal memory 16 stores therein various data such as control programs for performing transmission/reception of ultrasonic waves, image processing, and display processing; diagnostic information (patients' IDs and doctors' opinions, for example); a diagnostic protocol; and various body marks. The internal memory 16 is also used for storing the image data stored in the image memory 15, for example, as necessary. The data stored in the internal memory 16 can be transferred to an external device through an interface (not illustrated). The internal memory 16 also can store therein data transferred from the external device through the interface (not illustrated).

The control unit 17 controls the entire processing performed by the ultrasound diagnostic apparatus. Specifically, the control unit 17 controls processing performed by the transmitter/receiver 11, the B-mode processing unit 12, the Doppler processing unit 13, and the image generating unit 14 based on various setting requests input by the operator through the input device 3 and various control programs and data read from the internal memory 16. The control unit 17 also controls the monitor 2 to display ultrasonic image data for display stored in the image memory 15 and the internal memory 16.

The transmitter/receiver 11 and other units embedded in the apparatus body 10 may be configured by hardware such as integrated circuits and also may be computer programs modularized as software components.

The ultrasound diagnostic apparatus according to the first embodiment is an apparatus capable of performing contrast harmonic imaging (CHI) as ultrasound contrast imaging. The B-mode processing unit 12 described above can change detection frequency, thereby changing the frequency band to be imaged. With this function, the B-mode processing unit 12 separates reflected wave data in an imaging region of the subject P who is administered with an ultrasound contrast agent into reflected wave data of which the ultrasound contrast agent (microbubbles, bubbles) flowing in the imaging region is the reflection source and reflected wave data of which tissues present in the imaging region is the reflection source. This process enables generation of contrast image data performed by the image generating unit 14 in which flowing bubbles are imaged with high sensitivity.

A reflected wave signal from microbubbles includes a harmonic component of many nonlinear signals. Contrast image data is generated mainly based on a second harmonic (second-order harmonic) component. For example, the B-mode processing unit 12 separates reflected wave data into harmonic components and fundamental components by means of filter processing. However, there are some cases caused by the filter processing where the removal of fundamental components is not sufficiently performed, hindering generation of contrast image data in which the fundamental components are suppressed and the harmonic components are enhanced. In CHI, it is necessary to perform ultrasound transmission/reception with low acoustic pressure to prevent breakdown of microbubbles. However, in imaging performed by transmission/reception of ultrasound waves with low acoustic pressure, the signal/noise (S/N) ratio of contrast image data is lowered.

In contrast, phase modulation (PM), amplitude modulation (AM), and amplitude modulation/phase modulation (AMPM) are known as ultrasound transmission/reception methods that can improve the S/N ratio of contrast image data even in transmission/reception of ultrasound waves with low acoustic pressure. The ultrasound diagnostic apparatus according to the first embodiment is an apparatus capable of performing AM, PM, and AMPM.

In AM, in accordance with a scan sequence set by the control unit 17, the transmitter/receiver 11 causes ultrasound waves to be transmitted three times for each scanning line with the amplitude ratio thereof modulated to be "1:2:1", such as (0.5, 1, 0.5), in the same phase polarity. The transmitter/receiver 11 then outputs three pieces of reflected wave data to the B-mode processing unit 12. At this point, it is assumed that the pieces of reflected wave data of (0.5, 1, 0.5) are R1, R2, and R3. The B-mode processing unit 12 performs envelope demodulation on data on which addition and subtraction processing of "R1−R2+R3" has performed to generate B-mode data. The image generating unit 14 generates ultrasound image data from B-mode data for one frame or for one volume output from the B-mode processing unit 12.

In AMPM, in accordance with a scan sequence set by the control unit 17, the transmitter/receiver 11 causes ultrasound waves to be transmitted three times for each scanning line with the amplitude ratio thereof modulated to be "1:2:1", such as (−0.5, 1, −0.5), with the polarities inverted between the transmitted ultrasound waves in the first and the third times and the transmitted ultrasound waves in the second time. At this point, the pieces of reflected wave data of (−0.5, 1, −0.5) are denoted by R1, R2, and R3, respectively. The B-mode processing unit 12 performs envelope demodulation on data on which addition processing of "R1+R2+R3" has been performed to generate B-mode data. The image generating unit 14 generates ultrasound image data from B-mode data for one frame or for one volume output from the B-mode processing unit 12.

Figure 2:
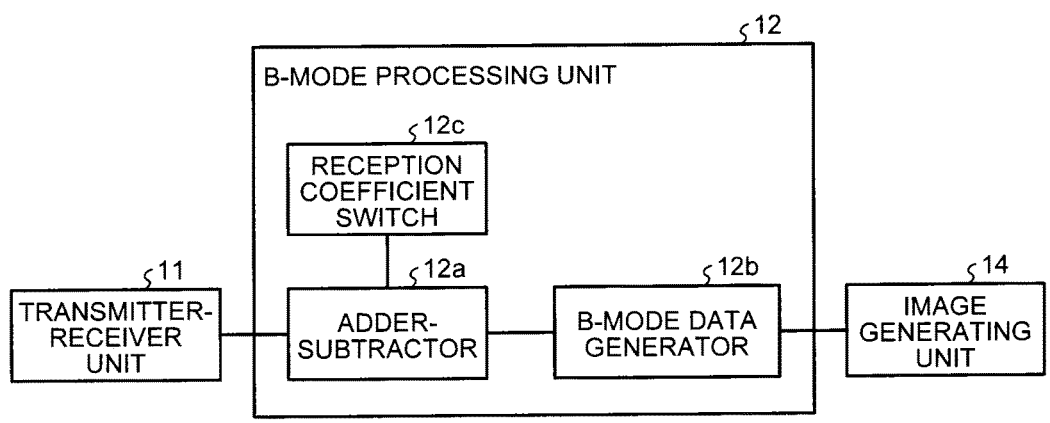
FIG. 2 is a block diagram illustrating a configuration example of a B-mode processing unit according to the first embodiment.
Figure 3A:
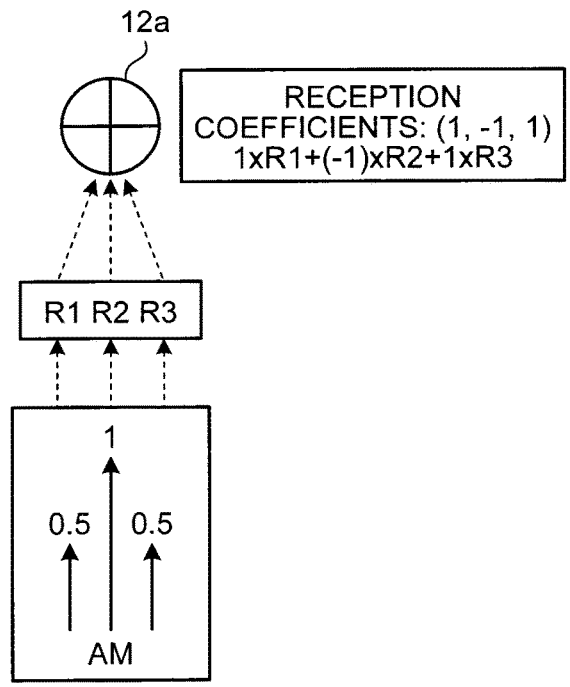
FIG. 3A is a diagram illustrating an example of processing performed by an adder/subtractor and a reception coefficients switch when AM is performed.
Figure 3B:
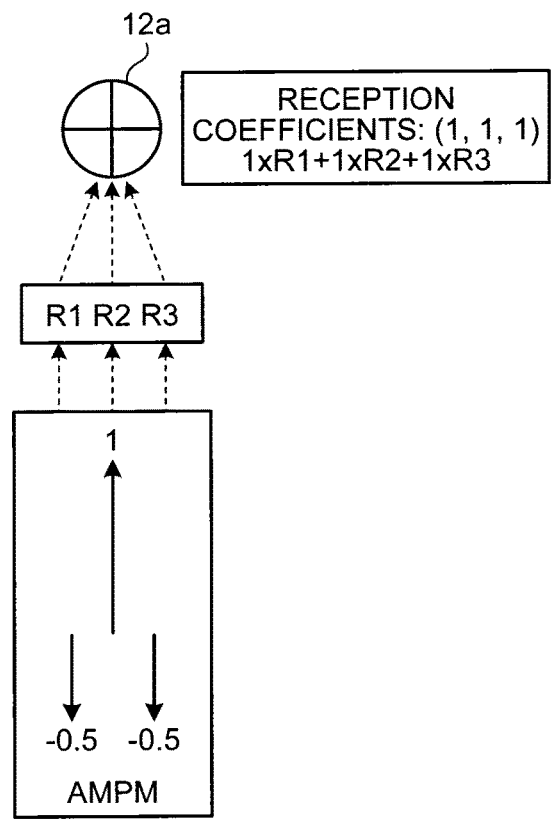
FIG. 3B is a diagram illustrating an example of processing performed by an adder/subtractor and a reception coefficients switch when AMPM is performed.

To perform AM and AMPM described above, the B-mode processing unit 12 according to the first embodiment is configured as illustrated in FIG. 2. FIG. 2 is a block diagram illustrating a configuration example of the B-mode processing unit according to the first embodiment. FIG. 3A is a diagram illustrating an example of processing performed by an adder/subtractor and a reception coefficients switch when AM is performed. FIG. 3B is a diagram illustrating an example of processing performed by an adder/subtractor and a reception coefficients switch when AMPM is performed.

As illustrated in FIG. 2, the B-mode processing unit 12 according to the first embodiment includes an adder/subtractor 12a, a B-mode data generator 12b, and a reception coefficients switch 12c. The adder/subtractor 12a and the reception coefficients switch 12c are processing units functioning when ultrasound transmission/reception are performed by AM and AMPM.

When AM of (0.5, 1, 0.5) is performed as illustrated in FIG. 3A, for example, the adder/subtractor 12a receives the reflected wave data "R1, R2, R3" output by the transmitter/receiver 11. The reflected wave data is IQ signals or RF signals having phase information. The reception coefficients switch 12c outputs reception coefficients (1, −1, 1) to the adder/subtractor 12a under the control of the control unit 17 when AM is performed. Based on the reception coefficients (1, −1, 1), the adder/subtractor 12a combines the three pieces of reflected wave data with "1×R1+(−1)×R2+1×R3" as illustrated in FIG. 3A. The adder/subtractor 12a then outputs the data thus combined to the B-mode data generator 12b. The B-mode data generator 12b generates B-mode data from the data thus combined and outputs the B-mode data to the image generating unit 14.

Furthermore, as illustrated in FIG. 3B, for example, the adder/subtractor 12a receives the reflected wave data "R1, R2, R3" output by the transmitter/receiver 11 when AMPM of (−0.5, 1, −0.5) is performed. When AMPM is performed, the reception coefficients switch 12c outputs reception coefficients (1, 1, 1) to the adder/subtractor 12a under the control of the control unit 17. Based on the reception coefficients (1, 1, 1), the adder/subtractor 12a combines the three pieces of reflected wave data with "1×R1+1×R2+1×R3" as illustrated in FIG. 3B. The adder/subtractor 12a then outputs the data thus combined to the B-mode data generator 12b. The B-mode data generator 12b generates B-mode data from the data thus combined and outputs the B-mode data to the image generating unit 14.

AM and AMPM are imaging methods that extract non-linear response of a contrast agent while canceling linear signals from tissues and specifically imaging the contrast agent. For this reason, in the case of ultrasound image data generated by AM and AMPM, tissue-originated signals are suppressed even if the ultrasound waves are with low acoustic pressure, creating contrast image data in which contrast agent-originated harmonic components are enhanced. In other words, performing AM or AMPM improves the S/N ratio.

Amplitude modulation is achieved by controlling transmission acoustic pressure or the number of transmission elements. However, due to the non-linearity of circuits configuring the transmitter/receiver 11, the tissue-originated signals are not completely canceled and remain. For example, in amplitude modulation using the number of transmission elements, transmission of ultrasound waves with small amplitude is achieved by transmission in an even or odd number of channels. When AM of (0.5, 1, 0.5) is performed, ultrasound transmission for the first "0.5" is performed in an even number of channels, ultrasound transmission for the second "1" is performed in all channels, and ultrasound transmission for the third "0.5" is performed in an odd number of channels. When AMPM of (−0.5, 1, −0.5) is performed, ultrasound transmission for the first "−0.5" is performed in an even number of channels, ultrasound transmission for the second "1" is performed in all channels, and ultrasound transmission for the third "−0.5" is performed in an odd number of channels.

However, due to circuit crosstalk during this transmission decimation, for example, the transmission acoustic pressure in "an even number of channels plus an odd number of channels" does not necessarily correspond to the transmission acoustic pressure in "all channels". Therefore, there are some cases where the amplitude ratio is not "1:2:1". In such a case, tissue signals remain.

Furthermore, when observing a microlesion, it is necessary to use an ultrasonic probe 1 with high frequency to obtain spatial resolution. This causes significant frequency dependent attenuation, reducing the sensitivity in a deep region. When scanning the subject P with a thick abdominal wall also, significant frequency dependent attenuation is caused, and therefore the sensitivity in a deep region is reduced. To improve the sensitivity in a deep region, frequency of transmitted ultrasound waves needs to be lowered although it lowers spatial resolution.

For this reason, techniques capable of improving the S/N ratio while achieving both spatial resolution and sensitivity in a deep region have been developed. With these techniques, the number of pieces of data to be transmitted and received on the same scanning line is increased to achieve both spatial resolution and sensitivity in a deep region. With the techniques, multiple ultrasound transmission/reception is performed by AM and AMPM near the same scanning line. The techniques enable improvement in sensitivity in a deep region while maintaining the S/N ratio and spatial resolution even when ultrasound transmission/reception with relatively high frequency, which causes high degree of attenuation in a deep region, are performed. It should be noted that the above-described techniques are hereinafter called "conventional techniques".

Sensitivity in a deep region can be improved with the "conventional techniques" with which the number of pieces of data is increased by repeating the same set of ultrasound transmission/reception. However, with the techniques, there are some cases where not only contrast agent-originated signals but tissue-originated signals (remaining components) are enhanced, spoiling the specific characteristics of the contrast agent. In other words, with the "conventional techniques", there are some cases where the bubble-tissue ratio is lowered.

From the background described above, to perform ultrasound contrast imaging with high bubble-tissue ratio and high sensitivity in a deep region, the transmitter/receiver 11 according to the first embodiment performs a first set of ultrasound transmission/reception and a second set of ultrasound transmission/reception, on a same scanning line of an imaging region of the subject P administered with a contrast agent, for a plurality of sets, to output reflected wave data for the plurality of the sets. It should be noted that the first set of ultrasound transmission/reception and the second set of ultrasound transmission/reception are performed near the same scanning line. Furthermore, the first set of ultrasound transmission/reception and the second set of ultrasound transmission/reception are performed alternately.

The first set of ultrasound transmission/reception is a scan sequence of performing amplitude-modulated ultrasound transmission transmitted a plurality of times and receiving reflected waves. Alternatively, the first set of ultrasound transmission/reception is a scan sequence of performing amplitude- and phase-modulated ultrasound transmission transmitted a plurality of times and receiving reflected waves. The second set of ultrasound transmission/reception is a scan sequence of receiving reflected waves by performing ultrasound transmission only whose phase modulation is different from phase modulation of the first set of ultrasound transmission/reception for the same number of times as ultrasound transmission performed in the first set of ultrasound transmission/reception. It should be noted that the number of the sets is to be an even number. The first set of ultrasound transmission/reception and the second set of ultrasound transmission/reception are scan sequences of receiving reflected waves by performing ultrasound transmission for multiple times. If the first set of ultrasound transmission/reception is performed once and the second set of ultrasound transmission/reception is performed once near the same scanning line, for example, two sets of ultrasound transmission/reception have been performed in total. If the first set of ultrasound transmission/reception is performed once, the second set of ultrasound transmission/reception is performed once, the first set of ultrasound transmission/reception is performed once, and the second set of ultrasound transmission/reception is performed once near the same scanning line, for example, four sets of ultrasound transmission/reception are performed in total.

The adder/subtractor 12a according to the first embodiment adds or subtracts reflected wave data for the plurality of sets. The image generating unit 14 according to the first embodiment generates contrast image data based on the data output from the adder/subtractor 12a. FIGS. 4, 5A, 5B, 5C, and 5D illustrate examples of ultrasound transmission/reception according to the first embodiment.

In the first scan sequence, the transmitter/receiver 11 performs, in the first set of ultrasound transmission/reception, amplitude modulation/phase modulation method that modulates both amplitudes and phases and performs, in the second set of ultrasound transmission/reception, amplitude modulation method that modulates only amplitudes. And, the transmitter/receiver 11 performs alternately and at least two sets in total, the first set of ultrasound transmission/reception and the second set of ultrasound transmission/reception. Furthermore, the transmitter/receiver 11 sets the same polarity for the transmitted ultrasound waves whose amplitude modulation is large in each of the first set of the ultrasound transmission/reception and the second set of the ultrasound transmission/reception, in the first scan sequence.

Figure 4:
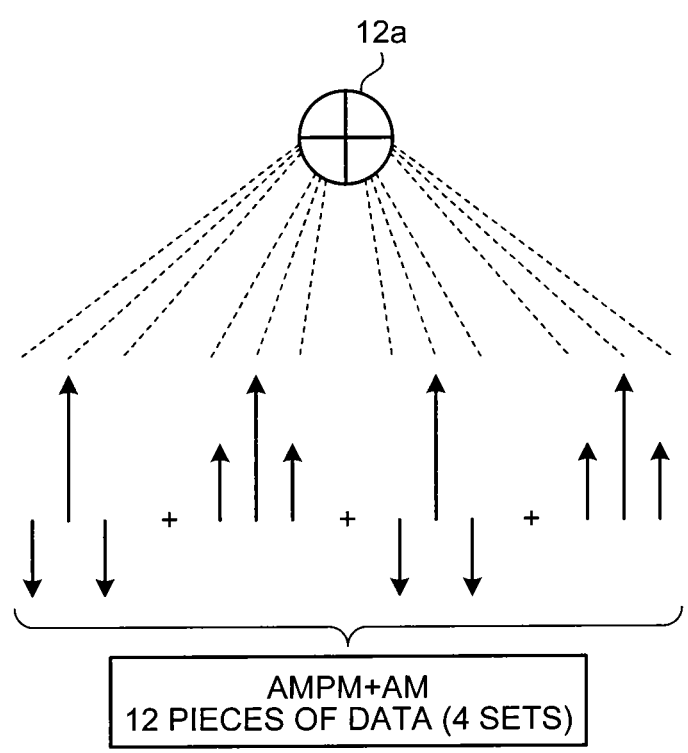
FIG. 4, FIG. 5A, FIG. 5B, FIG. 5C and FIG. 5D are diagrams illustrating an example of ultrasound transmission/reception according to the first embodiment.

FIG. 4 illustrates an example of the first scan sequence. In FIG. 4, AMPM of (−0.5, 1, −0.5) is to be the first set of ultrasound transmission/reception and AM of (0.5, 1, 0.5) is to be the second set of ultrasound transmission/reception. Furthermore, in the first scan sequence illustrated in FIG. 4, "AMPM+AM" is repeated twice, and thereby four sets in total of ultrasound transmission/reception are performed. With these processes, the transmitter/receiver 11 generates 12 pieces of reflected wave data.

The adder/subtractor 12a uses reception coefficients of (1, 1, 1) described above for reflected wave data of AMPM of (−0.5, 1, −0.5) and uses reception coefficients of (1, −1, 1) described above for reflected wave data of AM of (0.5, 1, 0.5), thereby combining the 12 pieces of reflected wave data.

As described above, due to circuit crosstalk in decimated transmission, for example, tissue signals remain. In the first scan sequence, the polarities of small amplitude are alternately inverted between the first set of ultrasound transmission/reception and the second set of ultrasound transmission/reception. This becomes the first scan sequence of preventing the tissue signals from remaining. Furthermore, in the first sequence, the polarity of large amplitude governing the behavior of a contrast agent is the same between the first set of ultrasound transmission/reception and the second set of ultrasound transmission/reception, which makes the first scan sequence a sequence of improving the sensitivity of the contrast agent.

In the second scan sequence, the transmitter/receiver 11 performs AMPM in the first set of ultrasound transmission/reception and performs AM in the second set of ultrasound transmission/reception as in the first scan sequence. Furthermore, in the second scan sequence, the transmitter/receiver 11 performs the first set of ultrasound transmission/reception and the second set of ultrasound transmission/reception for at least two sets alternately.

However, in the second scan sequence, the polarity of large amplitude is alternately inverted between the first set of ultrasound transmission/reception and the second set of ultrasound transmission/reception and the polarity of small amplitude is the same between the first set of ultrasound transmission/reception and the second set of ultrasound transmission/reception.

Figure 5A:
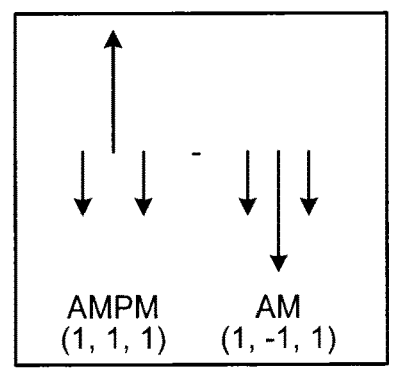

FIG. 5A illustrates an example of the second scan sequence in which the total number of the sets is "2". In FIG. 5A, AMPM of (−0.5, 1, −0.5) is to be ultrasound transmission/reception for the first set, and AM of (−0.5, −1, −0.5) is to be ultrasound transmission/reception for the second set. It should be noted that in FIGS. 5A to 5D values in parentheses are reception coefficients.

In the case illustrated in FIG. 5A, the adder/subtractor 12a combines reflected wave data for the first set using the reception coefficients of (1, 1, 1) with respect to the reflected wave data of AMPM of (−0.5, 1, −0.5) because it is AMPM. The adder/subtractor 12a also combines reflected wave data for the second set using the reception coefficients of (1, −1, 1) with respect to the reflected wave data of AM of (−0.5, −1, −0.5) because it is AM. In the case illustrated in FIG. 5A, the adder/subtractor 12a subtracts the reflected wave data for the second set from the reflected wave data for the first set. The second scan sequence is a sequence in which the polarity of small amplitude rate is set to the same and the remaining tissue signals are cancelled by subtracting the reflected wave data for the second set from the reflected wave data for the first set.

The adder/subtractor 12a may use the reception coefficients of (−1, 1, −1) with respect to the reflected wave data of AM of (−0.5, −1, −0.5), thereby adding the reflected wave data for the first set and the reflected wave data for the second set.

In the third scan sequence, the transmitter/receiver 11 inverts each of polarities of transmitted ultrasound waves performed for a plurality of times in the second set of the ultrasound transmission/reception from each of polarities of transmitted ultrasound waves performed for a plurality of times in the first set of the ultrasound transmission/reception. Specifically, as a case of the third scan sequence, there is a first case where both the first set of ultrasound transmission/reception and the second set are performed by AMPM and all polarities of the AMPM for the second set are inverted from the polarities of the AMPM for the first set. Furthermore, as a case of the third scan sequence, there is a second case where both the first set of ultrasound transmission/reception and the second set are performed by AM and all polarities of the AM for the second set are inverted from the polarities of the AM for the first set.

Figure 5B:
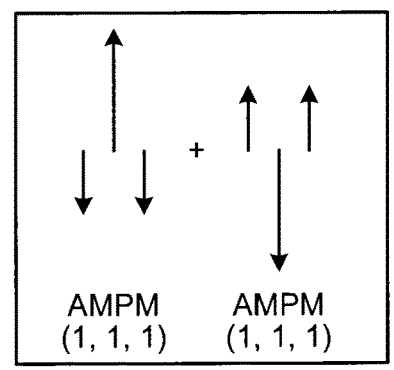

FIG. 5B illustrates an example of the third scan sequence performing the first case in which the total number of the sets is "2". In FIG. 5B, AMPM of (−0.5, 1, −0.5) is to be the first set of ultrasound transmission/reception and AMPM of (0.5, −1, 0.5) is to be the second set of ultrasound transmission/reception.

In the case illustrated in FIG. 5B, the adder/subtractor 12a combines reflected wave data for the first set using the reception coefficients of (1, 1, 1) with respect to the reflected wave data of AMPM of (−0.5, 1, −0.5) because it is AMPM. The adder/subtractor 12a also combines reflected wave data for the second set using the reception coefficients of (1, 1, 1) with respect to the reflected wave data of AMPM of (0.5, −1, 0.5) because it is AMPM. In the case illustrated in FIG. 5B, the adder/subtractor 12a adds the reflected wave data for the first set and the reflected wave data for the second set. In the third scan sequence performing the first case, the polarity of small amplitude is alternately inverted between the first set of ultrasound transmission/reception and the second set of ultrasound transmission/reception, becoming a sequence of preventing the tissue signals from remaining.

The adder/subtractor 12a may subtract the reflected wave data for the second set from the reflected wave data for the first set using reception coefficients of (−1, −1, −1) with respect to the reflected wave data of AMPM of (0.5, −1, 0.5).

Figure 5C:
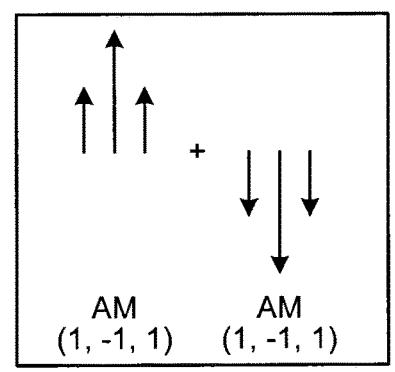

FIG. 5C illustrates an example of the third scan sequence performing the second case in which the total number of the sets performed is "2". In FIG. 5C, AM of (0.5, 1, 0.5) is to be the first set of ultrasound transmission/reception and AM of (−0.5, −1, −0.5) is to be the second set of ultrasound transmission/reception.

In the case illustrated in FIG. 5C, the adder/subtractor 12a combines reflected wave data for the first set using the reception coefficients of (1, −1, 1) with respect to the reflected wave data of AM of (0.5, 1, 0.5) because it is AM. The adder/subtractor 12a also combines reflected wave data for the second set using the reception coefficients of (1, −1, 1) with respect to the reflected wave data of AM of (−0.5, −1, −0.5) because it is AM. In the case illustrated in FIG. 5C, the adder/subtractor 12a adds the reflected wave data for the first set and the reflected wave data for the second set. In the third scan sequence performing the second case also, the polarity of small amplitude is alternately inverted between the first set of ultrasound transmission/reception and the second set of ultrasound transmission/reception, becoming a sequence of preventing the tissue signals from remaining.

Figure 5D:
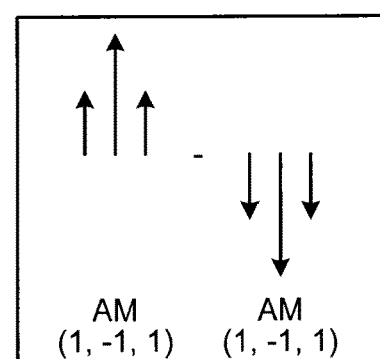

There are some cases where the response of the bubbles is weakened by the phase modulation between the sets although it depends on the transmission frequency. In particular, in the third scan sequence performing the second case, the phase modulation is large, and therefore the response of the bubbles is weakened with high possibility. For this reason, remains of tissue signals may be increased. However, to improve the sensitivity of the contrast agent intentionally, the reflected wave data for the second set may be subtracted from the reflected wave data for the first set as illustrated in FIG. 5D.

As for the first to the third scan sequences, a selection of an appropriate sequence as desired is possible depending on the transmission frequency and the type of the contrast agents. The sequence selection may be manually made by the operator or automatically set by the control unit 17, for example.

Figure 6:
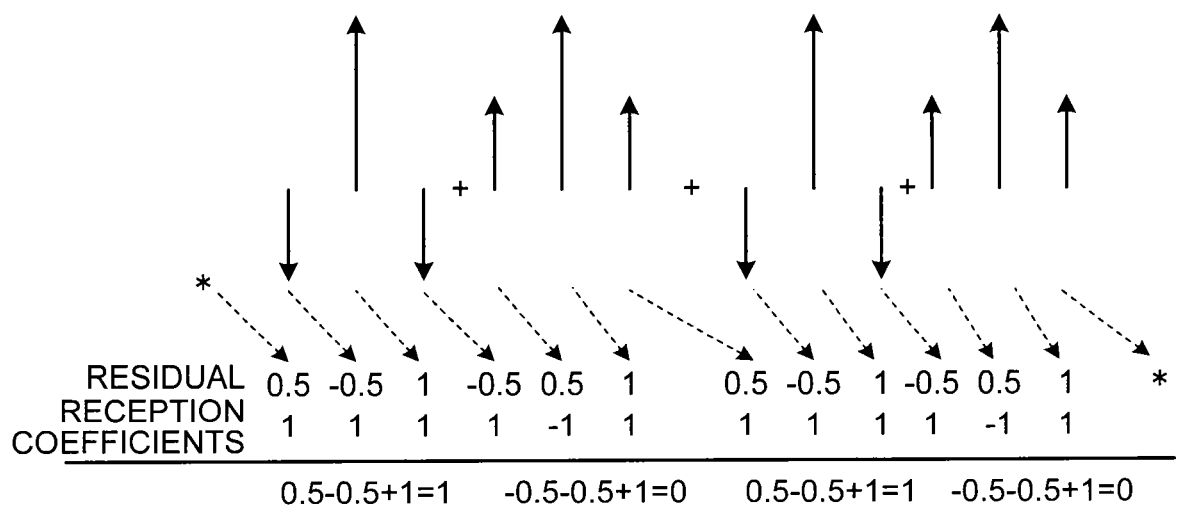
FIG. 6 is a diagram illustrating an example of a residual echo generated by combined use of AMPM and AM.

When using AMPM and AM in combination as in the first and the second scan sequences, artifacts due to residual echoes may be generated. Although contrast agents in the recent years can be imaged with low acoustic pressure, less influence is caused by artifacts due to residual echoes. However, when high echoes are present, multiple reflection may be caused and artifacts due to residual echoes becomes prominent. When AM without phase modulation is used for the second set, an echo in the previous transmission (a residual echo) enters in the current reception period and becomes an artifact as the residual echo fails to be cancelled. FIG. 6 is a diagram illustrating an example of a residual echo generated by combined use of AMPM and AM.

FIG. 6 is a diagram illustrating a residual echo generated when the first scan sequence illustrated in FIG. 4 is performed. As illustrated in FIG. 6, the residual echo in AM in the second set and the fourth set each is (−0.5, 0.5, 1). Because the reception coefficients are (1, −1, 1), each of the residual echoes in the second set and the fourth set is "−0.5−0.5+1=0" as illustrated in FIG. 6. In contrast, the residual echoes in AMPM in the first set and the third set are (0.5, −0.5, 1) as illustrated in FIG. 6. Because the reception coefficients are (1, 1, 1), each of the residual echoes in the first set and the third set is "0.5−0.5+1=1" as illustrated in FIG. 6. Specifically, in the first sequence, influence of the residual echoes is caused. In the second scan sequence also, influence of the residual echoes is caused similarly. In particular, when four or more sets in total of the first and the second scan sequences are performed, the influence of the residual echoes becomes larger.

Figure 7:
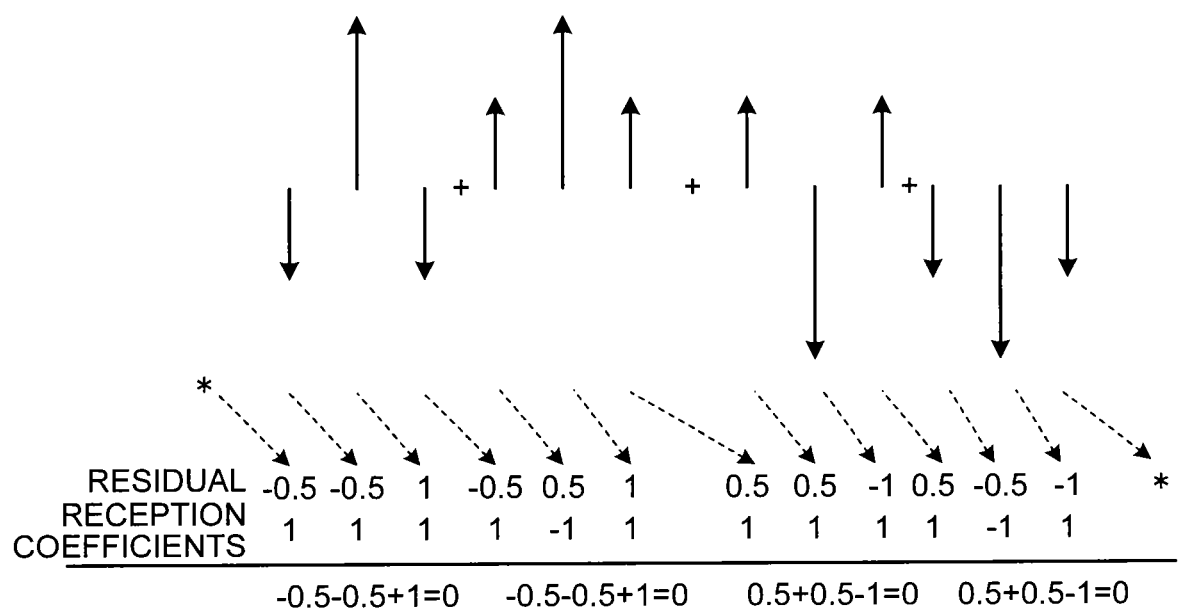
FIG. 7 is a diagram illustrating an example of ultrasound transmission/reception as a measure against residual echoes according to the first embodiment.

In the case of performing alternately four or more sets in total including the first set of ultrasound transmission/reception and the second set of ultrasound transmission/reception, the transmitter/receiver 11 inverts the transmission polarities between the first set of the ultrasound transmission/reception of an odd numbers of times and the first set of the ultrasound transmission of an even numbers of times. The transmitter/receiver 11 also inverts the transmission polarities between the second set of the ultrasound transmission/reception of an odd numbers of times and the second set of the ultrasound transmission/reception of an even numbers of times. FIG. 7 is a diagram illustrating an example of ultrasound transmission/reception as a measure against residual echoes according to the first embodiment.

FIG. 7 illustrates a case where the first scan sequence illustrated in FIG. 4 is a scan sequence as a measure against residual echoes. As illustrated in FIG. 7, AMPM for the third set (the second) is a sequence in which the AMPM for the first set (the first) is inverted and the AM for the fourth set (the second) is a sequence in which the AM for the second set (the first) is inverted.

As illustrated in FIG. 7, the residual echo in the AMPM in the first set is (−0.5, −0.5, 1). Because the reception coefficients are (1, 1, 1), the residual echo for the first set is "−0.5−0.5+1=0" as illustrated in FIG. 7. Furthermore, as illustrated in FIG. 7, the residual echo in the AM for the second set is (−0.5, 0.5, 1). Because the reception coefficients are (1, −1, 1), the residual echo for the second set is "−0.5−0.5+1=0" as illustrated in FIG. 7. The residual echo in the AMPM for the third set is (0.5, 0.5, −1) as illustrated in FIG. 7. Because the reception coefficients are (1, 1, 1), the residual echo for the third set is "0.5+0.5−1=0" as illustrated in FIG. 7. The residual echo in the AM for the fourth set is (0.5, −0.5, −1) as illustrated in FIG. 7. Because the reception coefficients are (1, −1, 1), the residual echo for the second set is "0.5+0.5−1=0" as illustrated in FIG. 7.

Specifically, the scan sequences illustrated in FIG. 7 can reduce the influence of the residual echoes. When the second scan sequence is a scan sequence as a measure against residual echoes, the influence of the residual echoes can be reduced by performing the same inversion as described above. However, in a scan sequence as a measure against residual echoes, the total number of the sets needs to be a multiple of 4.

Figure 8:
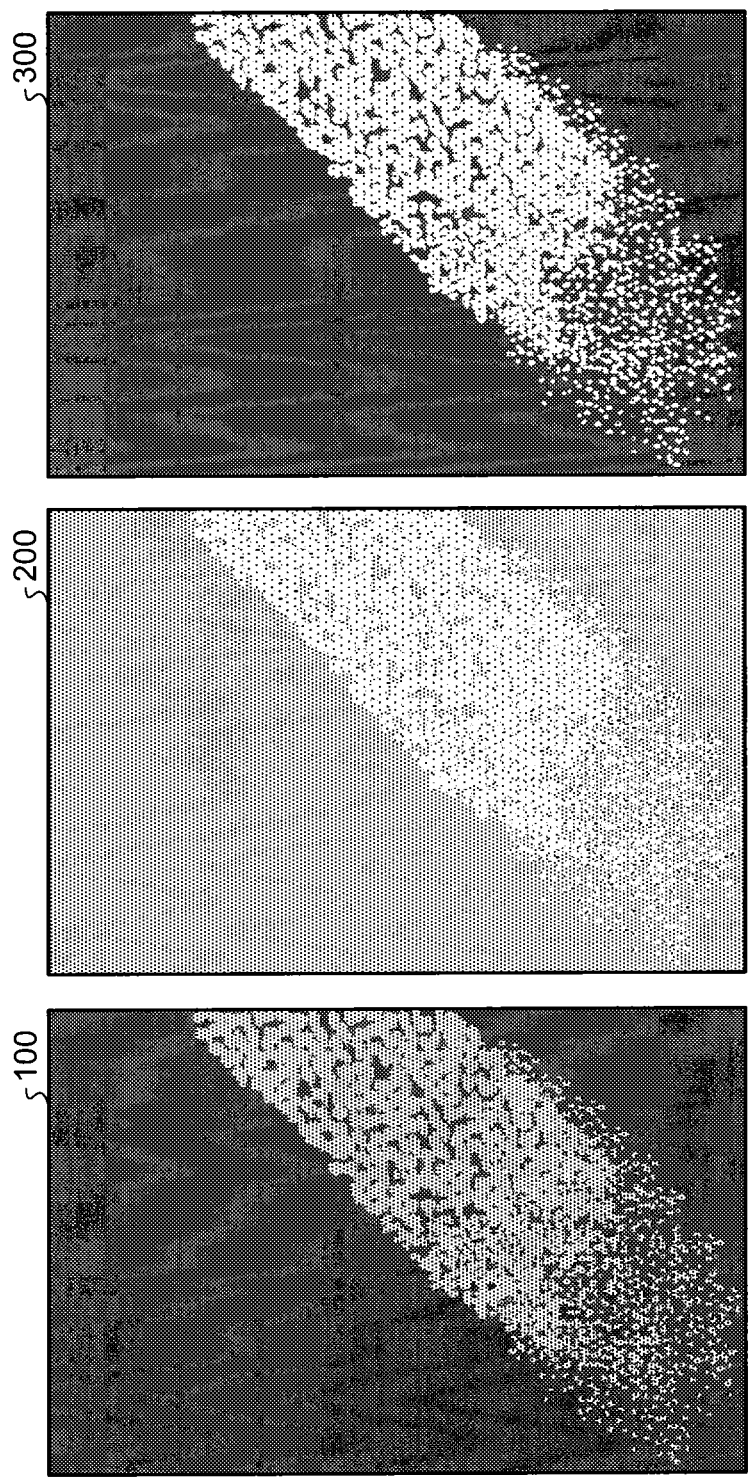
FIG. 8 is an example of the result of ultrasound contrast imaging performed by ultrasound transmission/reception according to the first embodiment.

FIG. 8 is an example of the result of ultrasound contrast imaging performed by ultrasound transmission/reception according to the first embodiment. The figure in the left in FIG. 8 illustrates a contrast image data 100 generated by a single AMPM and the figure in the center in FIG. 8 illustrates a contrast image data 200 generated by repeating AMPM four times (four sets) with the "conventional techniques". The figure in the right in FIG. 8 illustrates a contrast image data 300 generated by "AMPM+AM" illustrated in FIG. 4. When the contrast image data 100 and the contrast image data 200 are compared, the contrast image data 200 has the stronger signal intensity originated from a contrast agent to a deep region although the signal intensity originated from tissues is also strong on the whole. In contrast, the contrast image data 300 has strong signal intensity originated from a contrast agent to a deep region similarly to the contrast image data 200, and the signal intensity originated from tissues is suppressed to the same degree as in the contrast image data 100.

In the first embodiment, various scan sequences described above are used, and thereby increase of tissue-originated signals is suppressed as much as possible while ultrasound contrast imaging is performed with high bubble-tissue ratio and high sensitivity in a deep region. It should be noted that in the first embodiment, a case is applicable where the function of the reception coefficients switch 12c is incorporated as the function of the adder/subtractor 12a.

Second Embodiment

Figure 9:
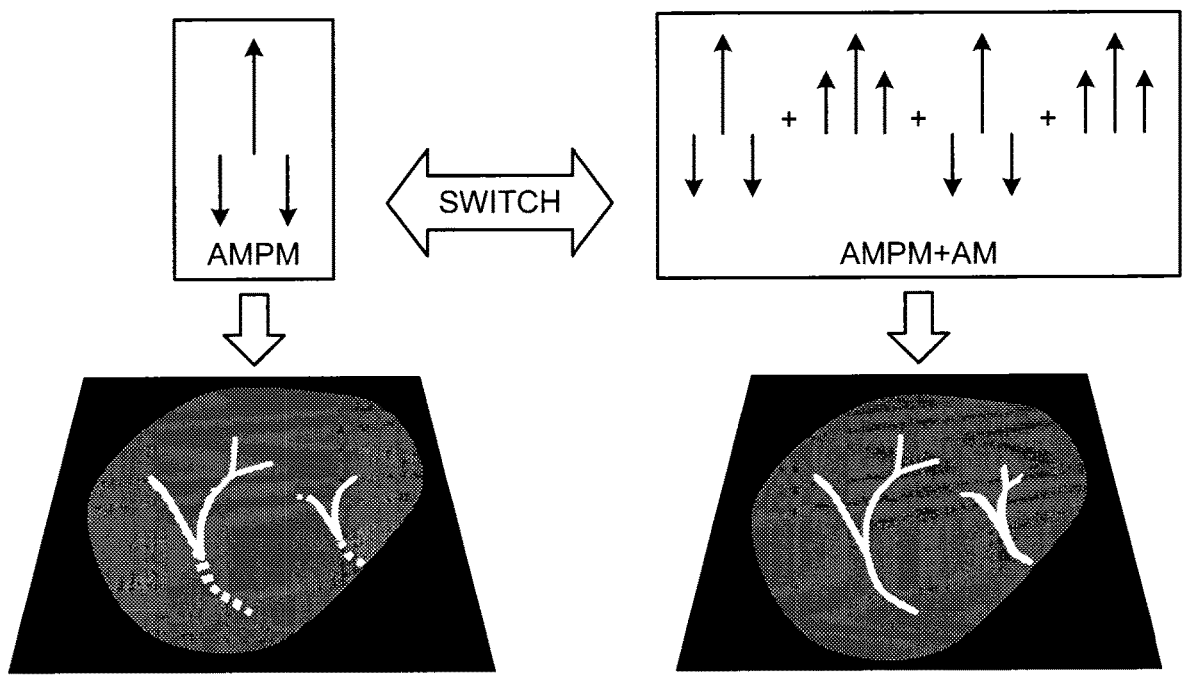
FIG. 9 is a diagram illustrating a second embodiment.

In a second embodiment, a case is described with reference to FIG. 9, for example, where a switching request made by the operator switches conventional ultrasound contrast imaging to the ultrasound contrast imaging described in the first embodiment. FIG. 9 is a diagram illustrating the second embodiment.

In the second embodiment, for performing ultrasound contrast imaging, the input device 3 receives a switch request to switch from a first mode in which one kind of ultrasound transmission/reception is performed to a second mode where a plurality of sets of the first set of ultrasound transmission/reception and the second set of ultrasound transmission/reception are performed alternately. The input device 3 also receives the number of the sets performed in the second mode.

In the second embodiment, the input device 3 receives a switching request from a first mode performing one kind of ultrasound transmission/reception for performing ultrasound contrast imaging to a second mode alternately performing a plurality of sets of the first set of the ultrasound transmission/reception and the second set of the ultrasonic transmission/reception. The input device 3 further receives a number of sets performed in the second mode.

For example, the operator performs ultrasound contrast imaging with "one set of AMPM" initially set as the first mode. With reference to the contrasted image in the first mode illustrated in the left figure in FIG. 9, when it is determined that the sensitivity of contrast imaging is poor in an observed depth, the operator operates a switch on a touch command screen included in the input device 3, for example, to input the switching request to switch to the second mode. For the second mode, the first scan sequence is initially set, for example. The operator sets the number of the sets performed in the second mode in accordance with the observed depth, for example. It should be noted that the operator may choose a suitable number of sets in view of the balance between observed depth and realtime performance. The operator also may choose a scan sequence in the second mode from various scan sequences described in the first embodiment.

The control unit 17 sets ultrasound transmission/reception conditions in the second mode when the input device 3 receives the switch request and the number of the sets. For example, when "AMPM+AM" illustrated in FIG. 4 is set, the control unit 17 sets the conditions of transmission/reception performed by the transmitter/receiver 11 based on the scan sequence of "AMPM+AM" with the number of the sets thus set. With this process, the operator can see the contrasted image in the second mode illustrated in the right figure in FIG. 9. In the contrasted image in the second mode illustrated in the right figure in FIG. 9, the sensitivity of contrast imaging in the observed depth is improved with the bubble-tissue ratio maintained compared with the contrasted image in the first mode.

In the second embodiment, the operator may switch again from the second mode to the first mode if the operator determines to give priority to realtime performance.

Figure 10:
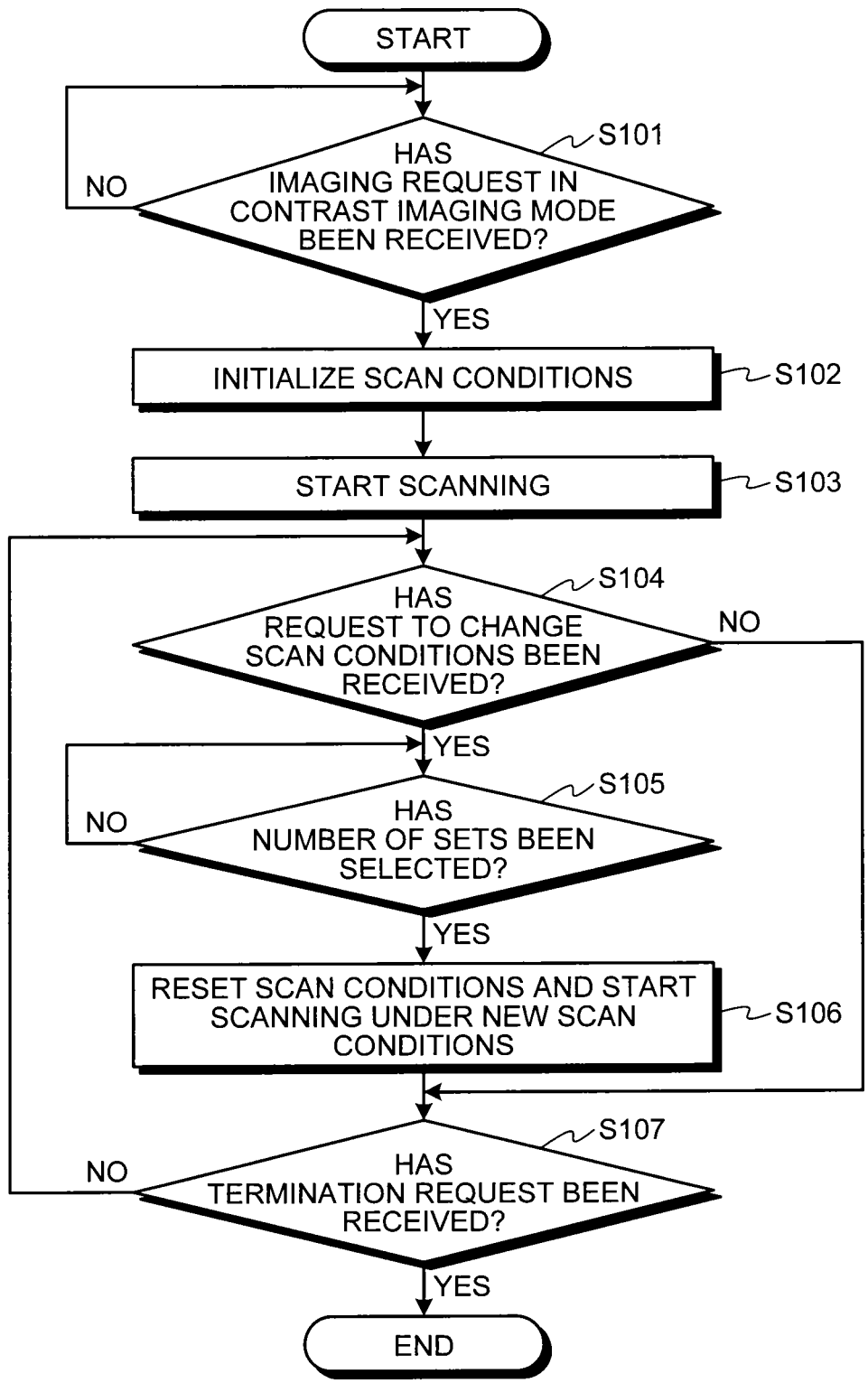
FIG. 10 is a flowchart illustrating an example of processing performed by an ultrasound diagnostic apparatus according to the second embodiment.

Next, an example of processing performed by the ultrasound diagnostic apparatus according to the second embodiment is described with reference to FIG. 10. FIG. 10 is a flowchart illustrating an example of processing performed by the ultrasound diagnostic apparatus according to the second embodiment.

As illustrated in FIG. 10, the control unit 17 in the ultrasound diagnostic apparatus according to the second embodiment determines if an imaging request in a contrast imaging mode has been received (Step S101). When the imaging request has not been received (No at Step S101), the control unit 17 waits until the request is received.

In contrast, when the imaging request has been received (Yes at Step S101), the control unit 17 initialize scanning conditions based on ultrasound transmission/reception in the first mode (Step S102) to start scanning in the first mode (Step S103).

The control unit 17 then determines if a request to change the scanning conditions has been received (Step S104). It should be noted that in Step S104 described above, the control unit 17 determines if a request to switch from the first mode to the second mode has been received. When the request to change the scanning conditions has been received (Yes at Step S104), the control unit 17 determines if the number of the sets performed in the second mode has been selected (Step S105).

When the number of the sets has not been selected (No at Step S105), the control unit 17 waits until the number of the sets are selected. In contrast, when the number of the sets has been selected (Yes at Step S105), the control unit 17 resets the scanning conditions to start scanning with the new scanning conditions (Step S106). In Step S106 described above, the control unit 17 starts scanning in the second mode.

After Step S106 or when the request to change the scanning conditions to the second mode has not been received (No at Step S104), the control unit 17 determines if a termination request has been received (Step S107). When the termination request has not been received (No at Step S107), the control unit 17 returns to Step S104 and determines if the request to change the scanning conditions has been received. When the control unit 17 returns to Step S104 because of No at Step S107 after Step S106, the control unit 17 determines if a request to switch from the second mode to the first mode has been received. After Yes at Step S104 because of the request to switch from the second mode to the first mode having been received, the number of the sets that the control unit 17 receives at Step S105 is "1" or a plural number (the number of the sets when the set transmission/reception is performed with the "conventional techniques"). Furthermore, the scanning started after the control unit 17 has reset the scanning conditions at Step S106 is a scanning in the first mode. It should be noted that when the number of the sets received after the request to switch from the second mode to the first mode has been received is a plural number, the control unit 17 may perform the second mode.

When the termination request has been received (Yes at Step S107), the control unit 17 terminates the processing.

As described above, in the second embodiment, a user interface switching between the first mode and the second mode in accordance with a request from the operator can be provided.

Third Embodiment

Figure 11:
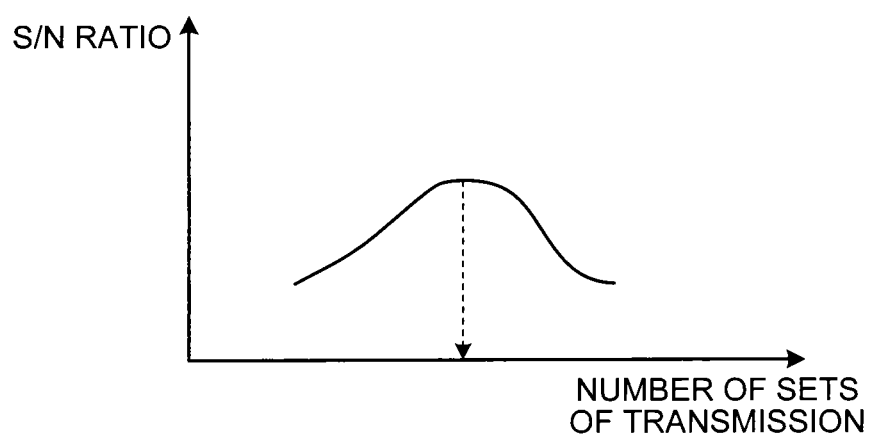
FIG. 11 is a diagram illustrating a third embodiment.

In a third embodiment, a case is described with reference to FIG. 11, for example, where the number of the sets of transmission in the second mode is automatically set when the first mode is switched to the second mode. FIG. 11 is a diagram illustrating a third embodiment.

The input device 3 according to the third embodiment receives a switching request to switch from the first mode to the second mode. The control unit 17 sets a number of transmission sets in the second mode based on a signal-to-noise ratio of contrast image data generated by changing a number of sets in the second mode when the input unit 3 receives the switching request.

By controlling the transmitter/receiver 11, the control unit 17 causes the image generating unit 14 to generate contrast image data in a case where ultrasound transmission/reception are performed with the number of the sets of transmission in the first scan sequence sequentially changed as "2, 4, 6 . . . " and contrast image data in a case where only ultrasound reception is performed and ultrasound transmission is not performed, for example. The control unit 17 calculates the S/N ratio for each set of transmission from a pair of contrast image data generated for each set of transmission. The control unit 17 then estimates the optimum number of the sets with which the S/N ratio is the highest as illustrated in FIG. 11. Thereafter, the control unit 17 sets the scanning conditions in the second mode in accordance with the optimum number of the sets. It should be noted that the control unit 17 may calculate the S/N ratio limiting to the region of interest that the operator has set in the B-mode image data, for example.

Figure 12:
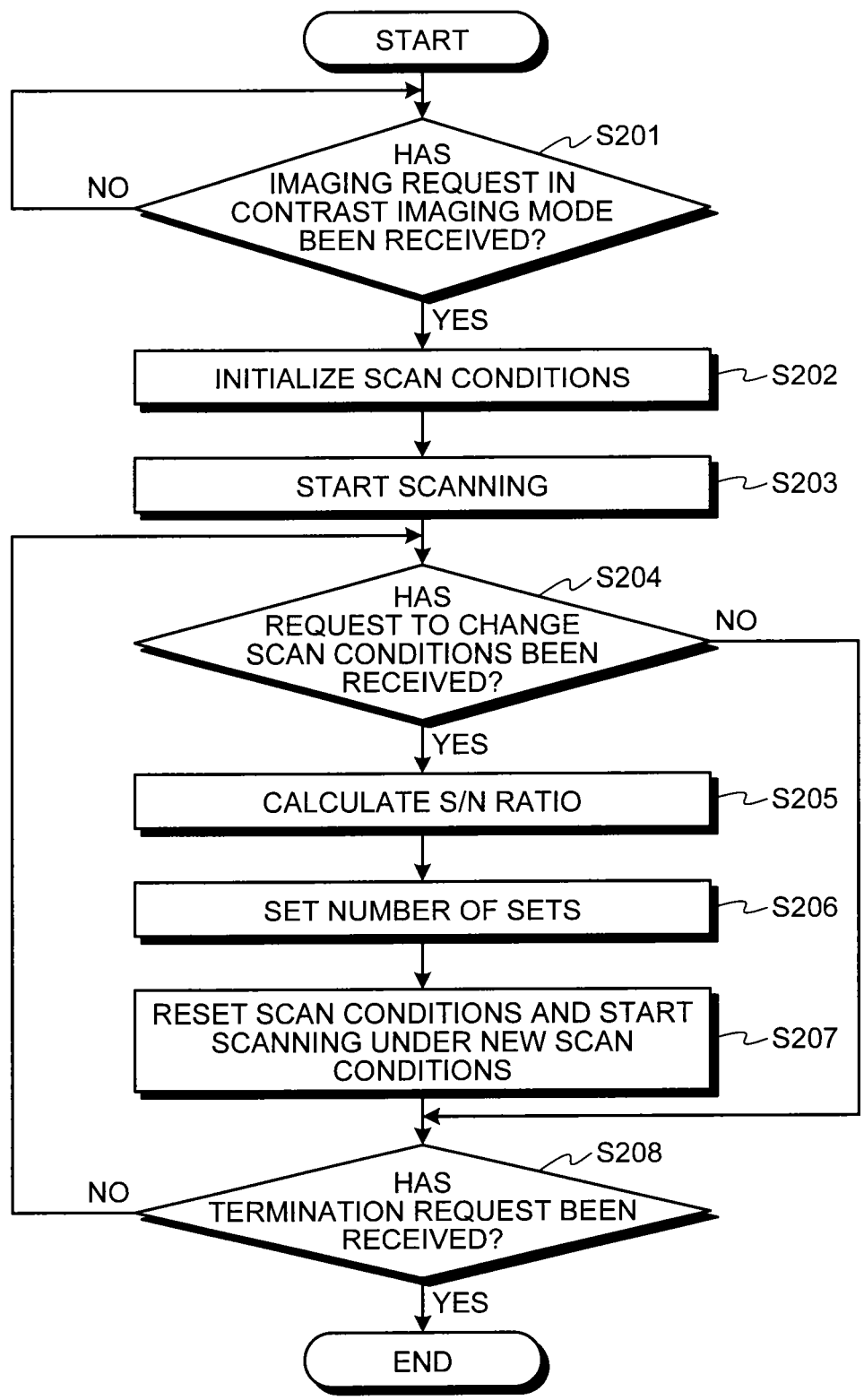
FIG. 12 is a flowchart illustrating an example of processing performed by an ultrasound diagnostic apparatus according to the third embodiment.

Next, an example of processing performed by the ultrasound diagnostic apparatus according to the third embodiment is described with reference to FIG. 12. FIG. 12 is a flowchart illustrating an example of processing performed by the ultrasound diagnostic apparatus according to the third embodiment.

As illustrated in FIG. 12, the control unit 17 of the ultrasound diagnostic apparatus according to the third embodiment determines if an imaging request in the contrast imaging mode has been received (Step S201). When the imaging request has not been received (No at Step S201), the control unit 17 waits until the request is received.

In contrast, when the imaging request in the contrast imaging mode has been received (Yes at Step S201), the control unit 17 initialize scanning conditions based on ultrasound transmission/reception in the first mode (Step S202) to start scanning in the first mode (Step S203).

The control unit 17 then determines if a request to change the scanning conditions has been received (Step S204). It should be noted that in Step S204 described above, the control unit 17 determines if a request to switch from the first mode to the second mode has been received. When the request to change the scanning conditions has been received (Yes at Step S204), the control unit 17 calculates the S/N ratio of the contrast image data while changing the number of the sets of transmission in the second mode (Step S205) and estimates the optimum number of the sets of transmission thereby setting the number of sets of the transmission (Step S206).

The control unit 17 resets the scanning conditions to start scanning with the new scanning conditions (Step S207). In Step S207 described above, the control unit 17 starts scanning in the second mode.

After Step S207 or when the request to change the scanning conditions has not been received (No at Step S204), the control unit 17 determines if a termination request has been received (Step S208). When the termination request has not been received (No at Step S208), the control unit 17 returns to Step S204 and determines if the request to change the scanning conditions has been received. When the control unit 17 returns to Step S204 because of No at Step S208 after Step S207, the control unit 17 determines if a request to switch from the second mode to the first mode has been received.

At this point, the S/N ratio calculated at Step S205 by the control unit 17 after the request to switch from the second mode to the first mode has been received is the S/N ratio of contrast image data in a case where the number of the sets of transmission in one kind of AMPM is changed, for example. Furthermore, when the number of the sets of transmission set at Step S206 by the control unit 17 after the request to switch from the second mode to the first mode has been received is a plural number, the scanning started with the scanning conditions reset at Step S207 is a scanning in the first mode with the "conventional techniques". It should be noted that after the request to switch from the second mode to the first mode has been received, the control unit 17 may calculate the S/N ratio in the second mode as well as in the first mode at Step S205 and reset the scanning conditions in accordance with the number of the sets for performing the set transmission/reception in the second mode at Step S206, based on the calculation result. In that case, the scanning started after the scanning conditions have been reset at Step S207 is a scanning in the second mode.

On the other hand, when the termination request has been received (Yes at Step S208), the control unit 17 terminates the processing.

As described above, in the third embodiment, the number of the sets of transmission in the second mode is automatically set, and thereby the burden on the operator can be reduced when switching to the second mode.

Fourth Embodiment

Figure 13:
FIG. 13, FIG. 14 and FIG. 15 are diagrams illustrating a fourth embodiment.
Figure 14:
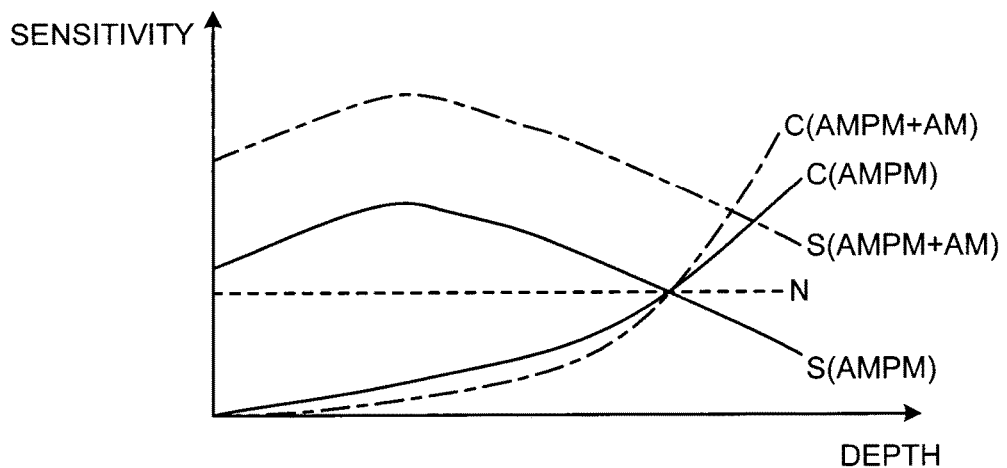
Figure 15:
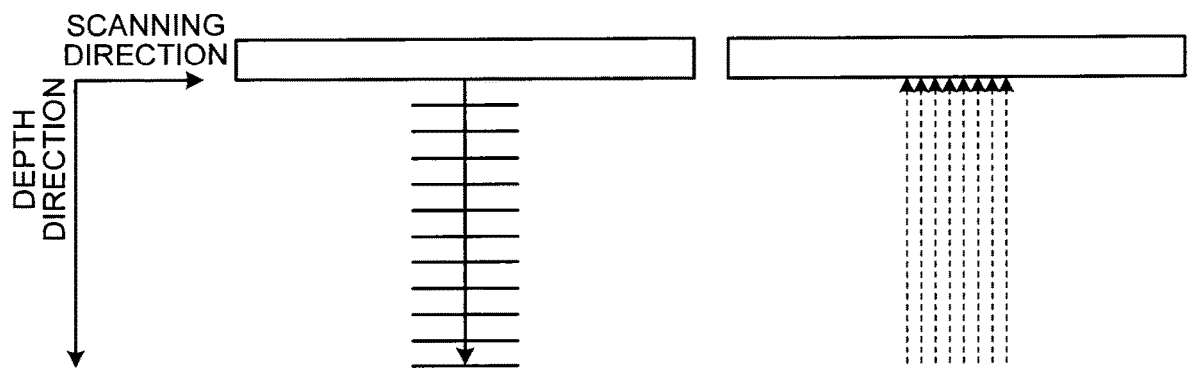

In a fourth embodiment, three modifications in the first to the third embodiments described above are explained with reference to FIGS. 13 to 15. FIGS. 13 to 15 are diagrams illustrating the fourth embodiment.

First, the first modification is described. In the second embodiment, the total number of the sets of the first set of ultrasound transmission/reception and the second set of ultrasound transmission/reception is manually set. In the third embodiment, the total number of the sets of the first set of ultrasound transmission/reception and the second set of ultrasound transmission/reception is automatically set to the optimum number of the sets estimated in accordance with the S/N ratio. In each case, the sensitivity of contrasted imaging in a deep region is improved with the bubble-tissue ratio maintained.

The transmitter/receiver 11 according to the first modification adjusts the transmission output of ultrasound waves in accordance with the total number of the sets. Specifically, the transmitter/receiver 11 lowers the transmission acoustic pressure in accordance with the total number of the sets. For example, the transmitter/receiver 11 lowers the transmission acoustic pressure in accordance with the optimum number of the sets estimated from calculation of the S/N ratio, as illustrated in FIG. 13. Alternatively, the transmitter/receiver 11 lowers the transmission acoustic pressure in accordance with the number of the sets set by the operator.

In the first modification, the possibility that a contrast agent is broken down can be reduced by lowering the acoustic pressure when the sensitivity of contrast imaging in a deep region is improved with the bubble-tissue ratio maintained.

Next, the second modification is described. Generally speaking, reflected waves have different intensities depending on the depth of the reflection source thereof even if they have the same reflection source. Specifically, the deeper the position of the reflection source is, the intensity of the reflected wave is attenuated. For this reason, in conventional ultrasound diagnostic apparatuses, sensitivity correction is performed in which the gain is gradually increased in proportion to the depth direction, that is, the reception time. The gain correction described above is called sensitivity time control (STC). STC is performed by an amplifier circuit included in the transmitter/receiver 11 based on the setting input by the operator, for example.

In the AMPM, which is the first mode, bubble-originated signals "S(AMPM)" are in an upward-convex form having a peak near transmission focus in the depth direction as illustrated in FIG. 14. Furthermore, in AMPM, system noise "N" is substantially constant along the depth direction as illustrated in FIG. 14. In contrast, in "AMPM+AM" in the first scan sequence, which is the second mode, bubble-originated signals "S(AMPM+AM)" are higher than "S(AMPM)" with "N" maintained, as illustrated in FIG. 14.

In other words, the S/N ratio in the second mode is more improved than the S/N ratio in the first mode in the depth. In the second modification, the amplifier circuit included in the transmitter/receiver 11 adjusts the gain in the depth direction in accordance with the total number of the sets. Specifically, the amplifier circuit adjusts the shape of the gain curve "C(AMPM)" in AMPM under the control of the control unit 17. With this process, the amplifier circuit sets the gain curve "C(AMPM+AM)" in "AMPM+AM". More specifically, the amplifier circuit increases the gain in the depth of "C(AMPM)" to set "C(AMPM+AM)" because increasing the gain in the depth does not enhance the noise.

For example, when the optimum number of the sets is estimated by the control unit 17, the S/N ratio in the depth direction with the optimum number of the sets has been calculated. The control unit 17 sets the shape of C(AMPM+AM) in the depth from the S/N ratio in the depth direction thus calculated within the range in which the noise in a deep region is not enhanced and notifies the amplifier circuit of the shape.

Furthermore, in "AMPM+AM", bubble-originated signals are improved even in a shallow region, as illustrated in FIG. 14. For this reason, when gain correction is performed with "C(AMPM)", on the contrary, the luminance may be saturated in a shallow region, reducing the visibility of contrasted image signals. Therefore, the amplifier circuit may set "C(AMPM+AM)", which is "C(AMPM)" with the gain lowered in a shallow region so that the luminance will not be saturated.

Next, the third modification is described. In various scan sequences in the second mode described in the first embodiment, a plurality of ultrasound transmission/reception is performed on one scanning line, and therefore the frame rate is lowered. From this background, the transmitter/receiver 11 performs parallel simultaneous reception processing using plane waves or diffuse waves as transmitted ultrasound waves in the third modification.

FIG. 15 illustrates a case where eight-beam parallel simultaneous reception is performed with plane waves. In FIG. 15, a center axis in the depth direction of the plane waves transmitted is indicated by a solid arrow and reflected wave beams received simultaneously in the first time are indicated by broken arrows. The transmitter/receiver 11 receives reflected wave signals on eight scanning lines in ultrasound transmission/reception in the first time as illustrated in FIG. 15. With this process, the transmitter/receiver 11 can generate data with the reflected waves on the eight scanning lines with one ultrasound transmission/reception process. Therefore, in the third modification, when various scan sequences in the second mode are performed, lowering of the frame rate can be prevented.

The ultrasound imaging methods described in the first to the fourth embodiments described above can be achieved by executing ultrasound imaging programs prepared in advance in a computer such as a personal computer or a work station. These ultrasound imaging programs can be distributed via a network such as the Internet. Furthermore, the ultrasound imaging programs can be executed, being stored in a computer-readable non-transitory recording medium such as a hard disc, a flexible disc (FD), a CD-ROM, an MO, and a DVD, and being read out from the non-transitory recording medium by the computer.

As described above, according to the first to the fourth embodiments, ultrasound contrast imaging can be performed with high bubble-tissue ratio and with high sensitivity in a deep region.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus, comprising:
a transmitter and a receiver configured to perform a first set of ultrasound transmission and reception and a second set of ultrasound transmission and reception, on a same scanning line of an imaging region of a subject administered with a contrast agent, for a plurality of sets, to output reflected wave data for the plurality of the sets,
the first set of the ultrasound transmission and reception performing amplitude-modulated or amplitude- and phase-modulated ultrasound transmission transmitted a plurality of times and receiving reflected waves, and
the second set of the ultrasound transmission and reception being transmission and reception whose phase modulation being different from phase modulation of the first set of the ultrasound transmission and reception;
an adder or a subtractor configured to add or subtract, respectively, the reflected wave data for the plurality of the sets and output a result of the added or subtracted reflected wave data as data; and
an image generating unit configured to generate contrast image data based on the data output from the adder or subtractor, wherein
the transmitter and receiver are configured to perform each transmission of the first set of ultrasound transmission and reception and each transmission of the second set of ultrasound transmission and reception alternately, wherein
when performing alternately four or more sets in total including the first set of ultrasound transmission and reception and the second set of ultrasound transmission and reception, the transmitter and receiver are configured to invert transmission polarities between the first set of the ultrasound transmission and reception of an odd number of times and the first set of the ultrasound transmission of an even number of times, and configured to invert transmission polarities between the second set of the ultrasound transmission and reception of an odd number of times and the second set of the ultrasound transmission and reception of an even number of times.

2. The ultrasound diagnostic apparatus according to claim 1, wherein the transmitter and the receiver are configured to perform, in the first set of the ultrasound transmission and reception, an amplitude modulation/phase modulation method that modulates both amplitudes and phases, and in the second set of the ultrasound transmission and reception, amplitude modulation method that modulates only amplitudes.

3. The ultrasound diagnostic apparatus according to claim 2, wherein the transmission and receiver are configured to set the same polarity for the transmitted ultrasound waves whose amplitude modulation is largest in each of the first set of the ultrasound transmission and reception and the second set of the ultrasound transmission and reception.

4. The ultrasound diagnostic apparatus according to claim 1, wherein the transmitter and receiver are configured to invert each of polarities of transmitted ultrasound waves performed for a plurality of times in the second set of the ultrasound transmission and reception from each of polarities of transmitted ultrasound waves performed for a plurality of times in the first set of the ultrasound transmission and reception.

5. The ultrasound diagnostic apparatus according to claim 1, further comprising:
an input unit configured to receive a switching request from a first mode to a second mode and that further receives a number of sets performed in the second mode, the first mode performing one kind of ultrasound transmission and reception for performing ultrasound contrast imaging, and the second mode alternately performing a plurality of sets of the first set of the ultrasound transmission and reception and the second set of the ultrasonic transmission and reception; and
a control unit configured to set conditions of ultrasound transmission and reception in the second mode when the input unit receives the switching request and the number of the sets.

6. The ultrasound diagnostic apparatus according to claim 1, further comprising:

an input unit configured to receive a switching request from a first mode to a second mode, the first mode performing one kind of ultrasound transmission and reception for performing ultrasound contrast imaging, and the second mode alternately performing a plurality of sets of the first set of ultrasound transmission and reception and the second set of ultrasonic transmission and reception; and a control unit configured to set a number of transmission sets in the second mode based on a signal-to-noise ratio of contrast image data generated by changing a number of sets in the second mode when the input unit receives the switching request.

7. The ultrasound diagnostic apparatus according to claim 1, wherein the transmitter and receiver are configured to perform parallel simultaneous reception processing using plane waves or diffuse waves as transmitted ultrasound waves.

8. The ultrasound diagnostic apparatus according to claim 1, wherein the transmitter and receiver are configured to adjust transmission output of ultrasound waves in accordance with a total number of sets of the first set of the ultrasound transmission and reception and the second set of the ultrasound transmission and reception.

9. The ultrasound diagnostic apparatus according to claim 1, wherein the transmitter and receiver are configured to adjust a gain in a depth direction in accordance with a total number of sets of the first set of the ultrasound transmission and reception and the second set of the ultrasound transmission and reception.

10. An ultrasound imaging method including:
performing, by a transmitter and a receiver, a first set of ultrasound transmission and reception and a second set of ultrasound transmission and reception, on a same scanning line of an imaging region of a subject administered with a contrast agent, for a plurality of sets, to output reflected wave data for the plurality of the sets,
the first set of the ultrasound transmission and reception performing amplitude-modulated or amplitude- and phase-modulated ultrasound transmission transmitted a plurality of times and receiving reflected waves, and
the second set of the ultrasound transmission and reception being transmission and reception at least whose phase modulation being different from phase modulation of the first set of the ultrasound transmission and reception;
adding or subtracting, by an adder or a subtractor, respectively, the reflected wave data for the plurality of the sets and outputting a result of the added or subtracted reflected wave data as data;
generating, by an image generating unit, contrast image data based on the data output from the adder or subtractor, wherein each transmission of the first set of ultrasound transmission and reception and each transmission of the second set of ultrasound transmission and reception are performed alternately; and
when performing alternately four or more sets in total including the first set of ultrasound transmission and reception and the second set of ultrasound transmission and reception, inverting transmission polarities between the first set of the ultrasound transmission and reception of an odd number of times and the first set of the ultrasound transmission of an even number of times, and inverting transmission polarities between the second set of the ultrasound transmission and reception of an odd number of times and the second set of the ultrasound transmission and reception of an even number of times.

11. An apparatus, comprising:
circuitry configured to
perform a first set of ultrasound transmission and reception and a second set of ultrasound transmission and reception, on a same scanning line of an imaging region of a subject administered with a contrast agent, for a plurality of sets, to output reflected wave data for the plurality of the sets,
the first set of the ultrasound transmission and reception performing amplitude-modulated or amplitude- and phase-modulated ultrasound transmission transmitted a plurality of times and receiving reflected waves, and
the second set of the ultrasound transmission and reception being transmission and reception whose phase modulation being different from phase modulation of the first set of the ultrasound transmission and reception,
add or subtract the reflected wave data for the plurality of the sets and output a result of the added or subtracted reflected wave data as data, and
generate contrast image data based on the data output, wherein
the circuitry is configured to perform each transmission of the first set of ultrasound transmission and reception and each transmission of the second set of ultrasound transmission and reception alternately, and
when performing alternately four or more sets in total including the first set of ultrasound transmission and reception and the second set of ultrasound transmission and reception, the circuitry is configured to invert transmission polarities between the first set of the ultrasound transmission and reception of an odd number of times and the first set of the ultrasound transmission of an even number of times, and configured to invert transmission polarities between the second set of the ultrasound transmission and reception of an odd number of times and the second set of the ultrasound transmission and reception of an even number of times.

* * * * *